United States Patent
Heidemann et al.

(12) 
(10) Patent No.: US 6,288,273 B1
(45) Date of Patent: Sep. 11, 2001

(54) METHOD FOR PRODUCING SHELL CATALYSTS FOR CATALYTIC GAS-PHASE OXIDATION OF AROMATIC HYDROCARBONS

(75) Inventors: Thomas Heidemann, Weinheim; Thomas Cimniak, Ludwigshafen; Bernhard Ulrich, Bockenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/380,213
(22) PCT Filed: Feb. 12, 1998
(86) PCT No.: PCT/EP98/00778
  § 371 Date: Aug. 26, 1999
  § 102(e) Date: Aug. 26, 1999
(87) PCT Pub. No.: WO98/37967
  PCT Pub. Date: Sep. 3, 1998

(30) Foreign Application Priority Data

Feb. 27, 1997 (DE) .............................................. 197 07 946

(51) Int. Cl.$^7$ ................................................... C07C 51/16
(52) U.S. Cl. ......................... 562/542; 562/412; 562/888; 502/104; 502/113; 502/240
(58) Field of Search ...................................... 562/542, 412, 562/888; 502/104, 113, 240

(56) References Cited

U.S. PATENT DOCUMENTS

| | | |
|---|---|---|
| 3,565,829 | 2/1971 | Friedrichsen . |
| 3,684,741 | 8/1972 | Friedrichsen . |
| 3,926,846 | 12/1975 | Ono . |
| 4,007,136 | 2/1977 | Blechschmitt . |
| 4,096,094 | 6/1978 | Blechschmitt . |
| 4,203,904 | 5/1980 | Reynolds . |
| 4,284,571 | 8/1981 | Sato . |
| 4,481,304 | 11/1984 | Sato . |
| 5,116,586 | 5/1992 | Baacke . |

FOREIGN PATENT DOCUMENTS

| | | |
|---|---|---|
| 1 642 938 | 5/1971 | (DE) . |
| 1 769 998 | 2/1972 | (DE) . |
| 24 36 009 | 2/1976 | (DE) . |
| 25 46 268 | 4/1977 | (DE) . |
| 25 47 624 | 4/1977 | (DE) . |
| 2 948 163 | 1/1980 | (DE) . |
| 28 30 765 | 1/1980 | (DE) . |
| 40 38 109 | 6/1992 | (DE) . |
| 163 231 | 12/1985 | (EP) . |
| 286 448 | 10/1988 | (EP) . |

*Primary Examiner*—Paul J. Killos
(74) *Attorney, Agent, or Firm*—Keil & Weinkauf

(57) ABSTRACT

The invention relates to a method for producing gas-phase catalysts gas-phase oxidation of aromatic hydrocarbons into carboxylic acids and/or carboxylic acid anhydrides upon whose carrier material a coating containing catalytically active metal oxide is applied in the form of a shell, wherein a powder is initially produced from a solution and/or suspension of catalytically active metal oxides and the precursor compounds thereof or simply the precursor compounds in the presence or absence of auxiliary agents in order to produce the catalyst. Said powder is then applied, in the form of a shell, to the carrier in the presence or absence of auxiliary agents after or without previous conditioning and without previous thermal treatment to produce the catalyst. The carrier which is thus coated undergoes thermal treatment in order to produce catalytically active metal oxides.

10 Claims, No Drawings

METHOD FOR PRODUCING SHELL CATALYSTS FOR CATALYTIC GAS-PHASE OXIDATION OF AROMATIC HYDROCARBONS

The present invention relates to a process for producing coated catalysts for the catalytic gas-phase oxidation of aromatic hydrocarbons to give carboxylic acids and/or carboxylic anhydrides, on the support material of which a layer of catalytically active metal oxides is applied in the form of a shell, and also a process for the catalytic gas-phase oxidation of aromatic hydrocarbons to give carboxylic acids and/or carboxylic anhydrides using a gas comprising molecular oxygen in a fixed bed at elevated temperature and by means of one or more coated catalysts arranged in layers, where the support material of the coated catalysts has a layer of catalytically active metal oxides applied to it in the form of a shell.

It is known that many carboxylic acids and/or carboxylic anhydrides are prepared industrially by the catalytic gas-phase oxidation of aromatic hydrocarbons such as benzene, the xylenes, naphthalene, toluene or durene in fixed bed reactors, preferably tube-bundle reactors. For example, benzoic acid, maleic anhydride, phthalic anhydride, isophthalic acid, terephthalic acid or pyromellitic anhydride are obtained by such processes. For this purpose, in general, a mixture of a gas comprising molecular oxygen, for example air, and the starting material to be oxidized is passed through a multiplicity of tubes arranged in a reactor, in which tubes there is located a bed of. at least one catalyst. To regulate the temperature, the tubes are surrounded by a heat transfer medium, for example a salt melt. Despite this thermostatting, the formation of hot spots in which the temperature is higher than in the remaining part of the catalyst bed can occur. These hot spots give rise to secondary reactions such as the total combustion of the starting material or lead to the formation of undesired by-products which can be separated from the reaction product only with great difficulty, if at all, for example the formation of phthalimide or benzoic acid in the preparation of phthalic anhydride (PA) from o-xylene. Furthermore, the formation of a pronounced hot spot when running up a plant obstructs a prompt increase of the loading of the gas fed to the reactor with xylene, since above a certain hot spot temperature the catalyst can be irreversibly damaged. For this reason, the xylene loading of the gas feed when running up the reactor can be increased only slowly, in small steps, to the xylene loading intended in the process, and this stepwise increase in loading has to be monitored very carefully.

To reduce the extent of the secondary reactions caused by hot spots, industrial practice has changed to arranging different active catalysts in layers in the catalyst bed. In such an arrangement, the less active catalyst is generally arranged in the fixed bed such that the reaction gas mixture comes into contact with it first, ie. it is located on the gas inlet side of the bed, whereas the more active catalyst is located toward the gas outlet from the catalyst bed. The different active catalysts in the catalyst bed can be exposed to the reaction gas at the same temperature, but the two layers comprising different active catalysts can also be thermostatted to different reaction temperatures for contact with the reaction gas.

Catalysts which have been found to be useful for these oxidation reactions are coated catalysts in which the catalytically active composition is applied in the form of a shell to a support material which is generally inert under the reaction conditions, for example quartz ($SiO_2$), porcelain, magnesium oxide, tin dioxide, silicon carbide, rutile, alumina ($Al_2O_3$), aluminum silicate, magnesium silicate (steatite), zirconium silicate or cerium silicate or mixtures of these. The catalytically active constituent of the catalytically active composition of these coated catalysts is generally titanium dioxide in the form of its anatase modification plus vanadium pentoxide. In addition, the catalytically active composition can comprise small amounts of many other oxidic compounds which as promoters influence the activity and selectivity of the catalyst, for example by decreasing or increasing its activity. Examples of such promoters are the alkali metal oxides, in particular lithium, potassium, rubidium and cesium oxide, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. Promoters which act to reduce the activity and increase the selectivity are, for example, the alkali metal oxides, whereas oxidic phosphorus compounds, in particular phosphorus pentoxide, increase the activity of the catalyst but reduce its selectivity.

According to the processes of DE-A 1642938 and DE-A 1769998, such coated catalysts are produced by spraying an aqueous and/or organic solvent-containing solution or suspension of the active composition constituents and/or their precursor compounds, which is hereinafter referred to as the "mix", onto the support material in a heated coating drum at elevated temperature until the amount of active composition as a proportion of the total weight of the catalyst has reached the desired figure. However, spraying results in high losses since considerable amounts of the mix are atomized and carried from the coating drum by the off-gas. Since the proportion of active composition in the total catalyst should generally deviate only slightly from the desired value because the amount of active composition applied and the thickness of the shell strongly influence the activity and selectivity of the catalyst, in the production method indicated the catalyst frequently has to be cooled, taken from the coating drum and weighed to determine the amount of active composition applied. If too much active composition is deposited on the catalyst support, a subsequent, gentle removal of the excess catalyst applied is generally not possible without impairing the strength of the shell, in particular without crack formation in the catalyst shell.

Further catalyst parameters which are important for oxidation reactions, namely the macroscopic structure of the active composition, for example its porosity and pore radius distribution, and also the chemical composition within the shell of active composition, can be influenced only with great difficulty in the abovementioned processes. The method of sequential spraying of mixes having different chemical compositions, as described in DE-A 2212964, does not lead to defined chemical compositions within the shell of active composition since chromatographic effects which occur during application in the heated coating drum lead to uncontrollable formation of concentration gradients of the active substances in the catalyst shell which result in a nonuniform chemical composition of the active composition in the catalyst shell and in the individual catalyst particles.

Gas-phase oxidations over the above-described coated catalysts take place not only on the outer surface of the shell. To achieve the catalyst activity and selectivity required for the complete reaction of the high starting material loadings in the reaction gas which are employed in industrial processes, efficient utilization of the total active composition shell of the catalyst and thus good accessibility for the reaction gas to the reaction centers located in this shell is necessary. Since the oxidation of aromatic compounds to give carboxylic acids and/or carboxylic anhydrides proceeds via many intermediate stages and the desired product can be further oxidized over the catalyst to give carbon dioxide and water, achievement of a high conversion of starting material with simultaneous suppression of the oxidative degradation of the desired product requires optimal matching of the residence time of the reaction gas in the active composition by generating a suitable, macroscopic active composition structure in the catalyst shell.

Furthermore, it has to be taken into account that the chemical composition of the gas at the outer surface of the active composition shell does not necessarily correspond to the chemical composition of the gas in the interior of the active composition. Rather, it has to be expected that the concentration of primary oxidation products is higher and the starting material concentration is lower than at the outer catalyst surface. This different chemical composition of gas should be taken into account by means of a targeted adjustment of the chemical composition within the shell of active composition in order to achieve optimum catalyst activity and selectivity.

EP-A 714 700 relates to a process for the preparation of a catalyst which consists of a support body and a catalytically active oxide composition applied to the surface of the support body, in which the support body is first moistened, as adhesive liquid, with an aqueous solution of an organic substance boiling above 100° C. at atmospheric pressure and then, by bringing into contact with a dry, finely divided active oxide composition, a layer of active oxide composition is adhered to the surface of the moistened support body and subsequently the adhesive liquid is removed from the moistened support body coated with active oxide composition. This process has the disadvantage that it necessitates a relatively high outlay in terms of time and effort and the abrasion resistance of the catalysts prepared is worthy of improvement.

DE-A 40 38 109 relates to a process for the preparation of shaped articles having a porous surface and narrow distribution of surface pore radii, and to the use of these shaped articles as support bodies for the attachment or immobilization of indicators, of catalysts, of biocomposition or of parts of the biocomposition. The shaped articles are coated, without use of pressure, without addition of a binder and at below 120° C., with small, uniform particles having a narrow particle size distribution of an agglome brable material such that the [lacuna] form between the small, uniform particles on the surface with a narrow distribution of pore radii. The shape and the size of the pore radii is determined here by the size of the small, uniform particles, and the distribution of the pore radii is determined by the particle size distribution. This process has similar disadvantages that have been shown with respect to EP-A 714 700. Moreover, the shaped articles coated in this manner do not withstand the technical and mechanical stresses of large-scale processes for the oxidation of aromatic compounds, as a result of which the mechanical stability changes on continuous operation and likewise the catalytic properties as a result of thermal sintering of the applied coating composition. DE-A 40 38 109 accordingly also contains no details on the utility of the shaped articles coated according to its process in processes for the large-scale oxidation of aromatic hydrocarbons.

It is an object of the present invention to find a process for producing coated catalysts for the catalytic gas-phase oxidation of aromatic hydrocarbons to give carboxylic acids and/or carboxylic anhydrides, which process both avoids the indicated disadvantages of the spraying process and of other coating processes of the prior art and makes possible, in a simple manner, the application of an amount of active composition which has been prescribed within narrow limits. Furthermore, this process should make it possible to influence the macroscopic active composition structure, for example its porosity and pore radius distribution, and also the chemical composition over the thickness of the catalyst shell and in this way enable catalysts having improved properties, such as improved mechanical stability and/or improved activity and/or selectivity, especially also during the running-up phase until reaching full-load operation of a plant for the gas-phase oxidation of aromatic compounds, to be produced.

We have found that this object is achieved by a process for producing coated catalysts for the catalytic gas-phase oxidation of aromatic hydrocarbons to give carboxylic acids and/or carboxylic anhydrides, on the support material of which a layer comprising catalytically active metal oxides is applied in the form of a shell, wherein a powder is first produced, by spray drying or freeze drying, from a solution and/or a suspension of the catalytically active metal oxides and their precursor compounds or these precursor compounds alone in the presence or absence of auxiliaries for catalyst production, the powder is subsequently applied as a paste in the form of a shell in the presence or absence of auxiliaries for catalyst production to the support after or without prior conditioning, without prior heat treatment to generate the catalytically active metal oxides and the support coated in this way is subjected to a heat treatment to generate the catalytically active metal oxides, the average layer thickness of the active composition of the coated catalysts produced in this way being from 10 to 250 μm.

The present invention further provides a process for the catalytic gas-phase oxidation of aromatic hydrocarbons to give carboxylic acids and/or carboxylic anhydrides in which the catalysts produced according to the present invention are used, and also the catalysts produced according to the invention.

Thus, in summary, the object of the present invention is achieved by first producing a powder comprising precursor compounds of the catalytically active metal oxides from the mix and subsequently using this powder to coat the catalyst support, if desired with the aid of auxiliaries. The coating of the support with a powder comprising exclusively catalytically active metal oxides but no precursor compounds of these metal oxides is thus not in accordance with the present invention.

The powder comprising the catalytically active metal oxides and their precursor compounds or these precursor compounds alone and employed for coating the catalyst support can be produced from the mix comprising these constituents by various methods, for example by spray drying or freeze drying, preferably by spray drying.

In the mix, the catalytically active metal oxides and their precursor compounds or these precursor compounds alone can be present in the form of suspended solid particles or in dissolved form. Preferably, these catalytically active components and their precursor compounds or these precursor compounds alone are present in the mix in the ratios in which they are later to be present in the catalytically active composition of the finished catalyst. However, it is also possible to add individual constituents of the catalytically active composition after production of the powder employed for coating the catalyst support and produced according to the present invention. Apart from the catalytically active constituents of the active composition and their precursor compounds or these precursor compounds alone, the mix can further comprise auxiliaries for catalyst production, for example binders and/or pore formers.

To prepare the mix, the active constituents of the catalyst, for example in the form of their oxides, salts such as nitrates, $C_1$–$C_{10}$-carboxylates, carbonates, hydrogencarbonates, sulfates, hydrogensulfates, halides or phosphates or as complexes such as oxalate or acetylacetone complexes, and also any auxiliaries used for catalyst production are dissolved, or if an individual material is not soluble, suspended in a solvent. Solvents or suspension media which can be used are water or organic liquids or mixtures of water with these liquids. Preference is given to using water or water in admixture with organic liquids, where the mixing ratio of water/organic liquid is generally not critical but preference is given to using those solvent mixtures containing 50 or more percent by weight of water.

As organic liquids, preference is given to using water-soluble solvents such as $C_1$–$C_4$-alcohols, water-soluble ethers, eg. tetrahydrofuran, dioxane or ethylene glycol dimethyl ether, water-soluble amides, eg. formamide, pyrrolidone, N-methylpyrrolidone or N,N-dimethylformamide, or water-soluble sulfoxides, eg. dimethyl sulfoxide.

Auxiliaries for catalyst production which can be added to the mix are binders, pore formers and/or temporary activity damping agents.

For the purposes of the present invention, the term binder refers to a substance which permanently or temporarily improves the adhesion of the powder particles of the active composition to one another and/or to the support material. Examples of binders which can be used in the process of the present invention are polyols such as ethylene glycol, propylene glycol, butylene glycols or glycerol or amides such as formamide, N,N-dimethylformamide, N,N-diethylformamide, N,N-dibutylformamide, acetamide, pyrrolidone or N-methylpyrrolidone.

The term pore former is used hereinafter to describe a substance which, by means of a volume change, for example by vaporization or decomposition during the heat treatment to generate the catalytically active metal oxides from their precursor compounds, effects, during the production of the coated catalyst, the formation in the active composition of a pore structure which is changed from that in an active composition to which no pore former has been added during its production. Pore formers which can be used in the process of the present invention are, for example, polyols such as glycerol or polymers such as cellulose, methylcellulose, cellulose acetate or starch or acids such as oxalic acid, tartaric acid or lactic acid or else amines such as melamine or amides such as urea. The type and amount of the auxiliaries to be added generally depends on the chemical composition of the active composition of the coated catalyst to be produced and is advantageously optimized in a preliminary experiment for the active composition having a particular chemical composition to be produced in each case.

For the purposes of the present invention, the term temporary activity damping agents refers to the abovementioned binders or pore formers or else all further auxiliaries which, for a limited period during the running-up phase of the reactor charged with the catalyst until it is in full load operation, lead to a targeted reduction in activity and/or to a lowering of the hot spot temperatures and thus aid the running-up procedure or the subsequent increase in the starting material loading of the gas stream fed to the catalyst without decreasing the mean catalytic activity or selectivity. These temporary activity damping agents are gradually decomposed at the temperatures at which the oxidation reactor is operated during running up and the increase in loading and thus gradually lose their action of lowering the activity of the catalyst. The temporary activity damping agents which can be present in the catalyst are, for example, polyols such as ethylene glycol, polymers such as cellulose or starch, or amines such as melamine.

Alternatively, these auxiliaries can also be mixed into the powder prepared according to the present invention from the mix. Likewise, it is possible to mix part of the auxiliaries into the mix and the remainder into the powder produced from the mix before or during the coating of the catalyst support with the powder from the mix.

To produce the powder comprising the active composition constituents and their precursor compounds or these precursor compounds alone by means of spray drying, the mix is generally sprayed to form small droplets from which the liquid is evaporated in concurrent or countercurrent by means of a stream of hot gas such as air, nitrogen, carbon dioxide, etc., preferably air. In this process, the dried, pulverulent solid particles comprising the active composition constituents and their precursor compounds or these precursor compounds alone can, depending on the structural configuration of the spray-drying apparatus, be separated out by gravity or by centrifugal force, for example using cyclones. For spray drying, it is usual to set a gas inlet temperature of the drying gas of from 250 to 450° C., preferably from 260 to 350° C., and to regulate the feed of drying gas and mix into the spray-drying apparatus such that the drying gas leaves the spray-drying apparatus at a temperature of generally from 100 to 200° C., preferably from 110 to 150° C. It is practical to carry out the spray drying at atmospheric pressure, but reduced pressure can also be advantageously used for drying. Spray drying can be carried out using commercial spray dryers, for example spray dryers from A/S Niro Atomizer, Copenhagen.

As an alternative to spray drying, the mix can be dried by means of freeze drying to form a powder. For this purpose, the mix is generally deep frozen on metal plates or belts cooled by means of liquid nitrogen or liquid air and the frozen solvent is sublimed from the frozen mix at subatmospheric pressure, producing a pulverulent product from the mix. Freeze drying of the mix can be carried out using commercial freeze-drying units, for example freeze-drying units from Leybold-Heraeus GmbH, Cologne.

The powders obtained by spray drying or freeze drying can, if desired, be additionally conditioned for the later coating of the catalyst, for example by setting a desired particle size distribution of the powder particles. This conditioning can be carried out by methods customary per se, eg. by sieving or air classification. Coarser particles can be comminuted to the desired particle size by milling, for example in ball or jet mills.

In general, the powder produced according to the invention is conditioned to particle sizes of from 0.1 to 100 $\mu$m, preferably from 0.5 to 80 $\mu$m and particularly preferably from 1.0 to 60 $\mu$m.

Using the powder produced in the manner described, which powder comprises the catalytically active metal oxides and their precursor compounds or these precursor compounds alone and possibly auxiliaries for catalyst production which have been added to the mix, the catalyst support is coated in conventional coating equipment, for example coating drums.

Support materials which can be used are virtually all support materials of the prior art as are advantageously employed in the production of coated catalysts for the oxidation of aromatic hydrocarbons to give carboxylic acids and/or carboxylic anhydrides, for example the support materials mentioned in the introduction in the discussion of the prior art. Advantageous support materials are, in particular, steatite and silicon carbide.

The form of the support material to be coated is generally not critical for the catalyst production process of the present invention. For example, it is possible to use catalyst supports in the form of spheres, rings, pellets, extrudates or granules.

Before coating the catalyst support, auxiliaries for catalyst production, eg. binders, pore formers or temporary activity damping agents, can be mixed into the powder from the mix or, if these auxiliaries have already been added to the mix, an additional amount of these auxiliaries can be mixed in. This addition can also be made during the coating process.

To coat the catalyst support, the powder produced according to the present invention is generally mixed with water and/or an organic liquid, advantageously an organic liquid which acts as binder, preferably only with water. In addition, further auxiliaries can be added to the liquid before it is mixed with the powder. The preparation of this paste can be carried out either within the coating apparatus in the presence of the catalyst support or separately outside the coating apparatus in a mixing apparatus, for example a stirring or kneading machine.

The coating of the catalyst support in the coating apparatus is generally carried out at from 10 to 50° C., preferably at room temperature.

The coated catalyst support is, in general, subsequently dried at from 20 to 200° C., preferably from 20 to 120° C. Drying can be carried out in the coating apparatus if this is heatable, or in conventional dryers. Drying can be carried out at atmospheric pressure or at subatmospheric pressure.

The catalyst production process of the present invention also makes it possible to produce coated catalysts in which the shell comprising the catalytically active constituents is built up of two or more layers having defined, different contents of active components. For this purpose, the catalyst support is first coated in the above-described manner with a layer having a defined composition consisting of the catalytically active metal oxides and their precursor compounds or these precursor compounds alone, this first layer is; then advantageously dried and, if desired, subjected to heat treatment, and a second layer or further layers is/are applied to the first layer in a similar way.

The average thickness of the layer of active composition in the coated catalysts produced according to the present invention for the gas-phase oxidation of aromatic compounds to give carboxylic acids and/or carboxylic anhydrides is generally from 10 to 250 $\mu$m, preferably from 50 to 200 $\mu$m and particularly preferably from 70 to 150 $\mu$m. The active composition of the coated catalysts produced according to the present invention generally has a BET surface area of from 1 to 100 $m^2/g$, preferably from 5 to 50 $m^2/g$ and particularly preferably from 7 to 30 $m^2/g$, determined by the method of Brunauer et al, J. Am. Chem. Soc. 60, 309 (1938). The pore volume of the active composition, determined by mercury porosimetry, is generally from 0.1 to 2.5 ml/g, preferably from 0.2 to 1.5 ml/g and particularly preferably from 0.3 to 1.1 ml/g, for the pores having pore diameters of from 1.7 to 400 nm.

The process of the present invention for producing coated catalysts for the gas-phase oxidation of aromatic hydrocarbons to give carboxylic acids and/or carboxylic anhydrides can be utilized for producing virtually all coated catalysts for this purpose. In particular, the process of the present invention enables the production of coated catalysts which have particularly advantageous properties and whose catalytically active composition comprises titanium dioxide in its anatase modification, oxidic compounds of vanadium, in particular vanadium pentoxide ($V_2O_5$), and also, if desired, oxidic promoters based on, for example, alkali metals, alkaline earth metals, thallium, aluminum, zirconium, iron, nickel, cobalt, manganese, tin, silver, copper, chromium, molybdenum, tungsten, iridium, tantalum, niobium, arsenic, antimony, cerium and/or phosphorus and whose catalytically active composition is applied in the form of a shell to a catalyst support comprising, for example, quartz, porcelain, magnesium oxide, silicon carbide, tin dioxide, rutile, alumina, aluminum silicate, magnesium silicate (steatite), zirconium silicate, cerium silicate or mixtures of these. For example, the process of the present invention can be used to produce coated catalysts having chemical compositions as are described in DE-A 2546268, EP-A 286448, DE-A 25 47 624, DE-A 2948163, EP-A 163231 or DE-A 2830765, the details concerning the chemical composition being hereby expressly incorporated by reference, with the coated catalysts produced according to the present invention having considerably improved catalytic properties in respect of yield, selectivity and/or running-up behavior compared with coated catalysts produced in a conventional way. The cause of this is not known. It is possible that the macroscopic structure of the active composition shell produced by the process of the present invention and/or the varied chemical composition of the active composition makes access of the starting material to the catalytically active centers in this active composition easier and at the same time makes possible a more rapid diffusion of the product formed out of the active composition shell before the product is further degraded by oxidation at the catalytically active centers. In addition, the low volatility of some auxiliaries, in particular the temporary activity damping agent, can lead to them being removed only slowly and being removed completely only during the course of the running-up of the reactor to full load operation and thus first reduce the catalyst activity by blocking of active centers. However, these attempts to explain the advantageous properties of the catalysts of the present invention are pure speculation since precise elucidation of these matters is not possible in practice.

The present invention further provides a process for the catalytic gas-phase oxidation of aromatic hydrocarbons to give carboxylic acids and/or carboxylic anhydrides using a gas comprising molecular oxygen in a fixed bed at elevated temperature and by means of one or more coated catalysts arranged in layers in the reactor, where the support material of the coated catalysts has a layer of catalytically active metal oxides applied to it in the form of a shell, wherein use is made of at least one coated catalyst which has been produced by coating a support, in the presence or absence of auxiliaries for catalyst production, with a powder which has been produced, by spray drying or freeze drying, from a solution and/or a suspension of the catalytically active metal oxides and their precursor compounds or these precursor compounds alone in the presence or absence of auxiliaries for catalyst production, after or without prior conditioning of the powder, and subsequent heat treatment of the support coated in this way to generate the catalytically active metal oxides.

The catalysts produced according to the present invention are preferably used for the gas-phase oxidation of aromatic $C_1$–$C_{10}$-hydrocarbons such as benzene, the xylenes, in particular ortho-xylene, toluene, naphthalene or durene (1,2,4,5-tetramethylbenzene) to give carboxylic acids and/or carboxylic anhydrides such as maleic anhydride, phthalic anhydride, benzoic acid and/or pyromellitic dianhydride. The process of the present invention is particularly preferably used for preparing phthalic anhydride from o-xylene.

For this purpose, the catalysts produced according to the present invention are introduced into reaction tubes thermostatted at the reaction temperature from the outside, for example by means of salt melts, and the reaction gas is passed over the catalyst bed thus prepared at generally from 300 to 450° C., preferably from 320 to 420° C. and particularly preferably from 340 to 400° C., and at a 40 gauge pressure of generally from 0.1 to 2.5 bar, preferably from 0.3 to 1.5 bar, at a space velocity of generally from 750 to 5000 $h^{-1}$.

The reaction gas fed to the catalyst is generally produced by mixing a gas comprising molecular oxygen, which gas can comprise not only oxygen but also suitable reaction moderators and/or diluents such as steam, carbon dioxide and/or nitrogen, with the aromatic hydrocarbon to be oxidized; the gas comprising molecular oxygen can contain generally from 1 to 100 mol %, preferably from 2 to 50 mol % and particularly preferably from 10 to 30 mol %, of oxygen, from 0 to 30 mol %, preferably from 0 to 10 mol %, of water vapor and also from 0 to 50 mol %, preferably from 0 to 1 mol %, of carbon dioxide, remainder nitrogen. To produce the reaction gas, the aromatic hydrocarbon to be oxidized is introduced into the gas comprising molecular oxygen in an amount of generally from 5 g to 120 g per standard $m^3$ of gas, preferably from 60 to 120 g/standard $m^3$ of gas and particularly preferably from 80 to 115 g/standard $m^3$ of gas.

The gas-phase oxidation is advantageously carried out with two or more zones, preferably two zones, of the catalyst bed present in the reaction tube being thermostatted to different reaction temperatures, for which purpose it is possible to use, for example, reactors having separate salt baths as are described in DE-A 2201528 or DE-A 2830765. If the reaction is carried out in two reaction zones, as described in DE-A 4013051, the reaction zone nearest the gas inlet for the reaction gas, which zone generally makes up from 30 to 80 mol % of the total catalyst volume, is generally thermostatted to a reaction temperature which is from 1 to 20° C., preferably from 1 to 10 ° C. and in particular from 2 to 8° C. higher than that of the reaction zone nearest the gas outlet. Alternatively, the gas-phase oxidation can also be carried out at one reaction temperature without division into temperature zones. Regardless of the temperature profile, the process is found to be particularly advantageous when the above-described reaction zones of the catalyst bed comprise catalysts which differ in their catalytic activity and/or the chemical composition of their active composition. When using two reaction zones, the catalyst used in the first reaction zone, ie. that nearest the gas inlet for the reaction gas, is one which has a somewhat lower catalytic activity than the catalyst present in the second reaction zone, ie. that closest to the gas outlet. In general, a catalyst whose catalytically active composition is doped with alkali metal oxides is used in the first reaction zone and a catalyst doped with phosphorus compounds is used in the second reaction zone. The composition of coated catalysts doped with alkali metal oxide is described, for example, in DE-A 2436009 while the composition of phosphorus-containing coated catalysts is described, for example, in DE-A 1769998; the further details in respect of the chemical composition provided in these references are, in the interests of simplicity, incorporated by reference.

In general, the reaction is controlled by setting the temperatures in such a way that the major part of the aromatic hydrocarbon present in the reaction gas is reacted with maximum yield in the first zone. The aromatic hydrocarbon is preferably reacted virtually completely with maximum yield in the first reaction zone.

If the process of the present invention is carried out using a plurality of reaction zones in which different catalysts are present, the coated catalysts produced according to the present invention can be used in all reaction zones. However, considerable advantages compared with conventional processes can generally be achieved even if a coated catalyst produced according to the present invention is used in only one of the reaction zones of the catalyst bed, for example the first reaction zone, and coated catalysts produced in a conventional way are employed in the other reaction zones, for example the second or last reaction zone.

The hydrocarbons used as starting material in the process of the present invention are constituents of petroleum and are isolated from the latter in petroleum refining.

Phthalic anhydride (PA) is produced worldwide on a large scale. PA is a starting material for producing plasticizers such as dioctyl phthalate. Pyromellitic dianhydride is used as a monomer in the production of polyimides.

EXAMPLES

Example 1

Production of the coated catalyst Ia—according to the present invention

A suspension comprising 250.0 g of anatase which had a BET surface area of 20 $m^2$/g (analysis: Ti: 59.8% by weight; S: 0.18% by weight, P: 0.09% by weight; Nb: 0.26% by weight; K: 0.008% by weight; Na: 0.02% by weight; Zr: 0.007% by weight; Pb: 0.011% by weight; W: 0.02% by weight; Sb: 0.01% by weight), 18.1 g of vanadyl oxalate, 1.43 g of cesium sulfate, 940 g of water and 122 g of formamide was spray dried in a spray dryer at a gas inlet temperature of 280° C. and a gas outlet temperature of the drying gas (air) of 120° C. to produce 270 g of powder having a particle size of from 3 to 60 um for 90% by weight of the powder. 700 g of steatite (magnesium silicate) rings having an external diameter of 8 mm, a length of 6 mm and a wall thickness of 1.5 mm were coated with 78 g of the powder and with addition of 56 g of a 30% by weight of water/70% by weight of glycerol mixture at 20° C. for 20 minutes in a coating drum. The catalyst support which had been coated in this way was subsequently dried at 100° C.

The weight of the catalytically active composition applied in this way was, after heat treatment at 400° C. for ½ hour, 10% by weight based on the total weight of the finished catalyst. The catalytically active composition applied, ie. the catalyst shell, consisted of 0.40% by weight of cesium (calculated as Cs), 4.0% by weight of vanadium (calculated as $V_2O_5$) and 95.6% by weight of titanium dioxide.

Example 2

Production of the coated catalyst Ib—according to the present invention

The catalyst was produced as described in Example 1, but 78 g of the powder were applied together with 56 g of a 43% by weight of water/43% by weight of glycerol/13% by weight of oxalic acid mixture to the support.

Example 3
Production of the coated catalyst Ic—according to the present invention The catalyst was produced as described in Example 1, but 78 g of the powder were first mixed with 4.1 g of melamine and subsequently applied to the support.

Example 4
Production of the coated catalyst Id—according to the present invention The catalyst was produced as described in Example 1, but use was made of a spray-dried powder having an altered vanadium content. First 39 g of a powder produced by a similar method to Example 1 (produced using 22.6 g of vanadyl oxalate in place of 18.1 g) and having a vanadium content of 5.0% by weight (calculated as $V_2O_5$) and subsequently 39 g of a powder produced by a method similar to Example 1 (produced using 13.6 g of vanadyl oxalate in place of 18.1 g) and having a vanadium content of 3.0% by weight (calculated as $V_2O_5$) were applied to the support.

Example 5
Production of the coated catalyst Ie—comparison 700 g of steatite rings having an external diameter of 8 mm, a length of 6 mm and a wall thickness of 1.5 mm were heated to 210° C in a coating drum and sprayed with a suspension of 250.0 g of anatase having a surface area of 20 $m^2/g$, 18.1 g of vanadyl oxalate, 1.43 g of cesium carbonate, 940 g of water and 122 g of formamide until the weight of the layer applied in this way corresponded to 10% of the total weight of the finished coated catalyst.

The catalytically active composition applied in this way, ie. the catalyst shell, consisted of 0.40% by weight of cesium (calculated as Cs), 4.0% by weight of vanadium (calculated as $V_2O_5$) and 95.6% by weight of titanium dioxide. 580 g of mix were required for coating the support, ie. about 31% of the mix sprayed in was lost by discharge from the drum during application.

Example 6
Production of catalyst II—not according to the present invention 700 g of steatite (magnesium silicate) rings having an external diameter of 8 mm, a length of 6 mm and a wall thickness of 1.5 mm were heated to 2100 in a coating drum and sprayed with a suspension of 400.0 g of anatase having a BET surface area of 20 $m^2/g$, 57.6 g of vanadyl oxalate, 14.4 g of antimony trioxide, 2.5 g of ammonium hydrogen phosphate, 0.65 g of cesium sulfate, 618 g of water and 128 g of formamide until the weight of the layer applied corresponded to 10.5% of the total weight of the finished catalyst.

The catalytically active composition applied in this way, ie. the catalyst shell, consisted of 0.15% by weight of phosphorus (calculated as P), 7.5% by weight of vanadium (calculated as $V_2O_5$), 3.2% by weight of antimony (calculated as $Sb_2O_3$), 0.1% by weight of cesium (calculated as Cs) and 89.05% by weight of titanium dioxide.

Examples 7–10
Preparation of phthalic anhydride—according to the present invention An iron tube having a length of 3.85 m and an internal diameter of 25 mm was charged in each of the individual experiments with a 1.60 m high bed of one of the catalysts Ia to Id and, on top of this, a 1.30 m high bed of the catalyst II. The iron tube charged with the catalysts was installed in such a way that the catalysts Ia to Id were in each case closest to the gas inlet, ie. came into contact with the feed gas first. The iron tube was thermostatted by means of a salt melt. 4.0 standard $m^3$/h of air having a continuously rising loading of 98.5% strength by weight o-xylene from 0 at the beginning to 80 g of o-xylene/standard $m^3$ of air at the end were passed through the tube from the top downwards at a gauge pressure of about 0.4 (i 0.05) bar. This gave the results summarized in the table below.

| Example: Catalyst combination | Salt bath temperature (° C.) | Maximum PA yield (% by weight) | Running-up time (d) |
|---|---|---|---|
| 7:Ia/II | 356 | 113.2 | 17 |
| 8:Ib/II | 351 | 114.2 | 24 |
| 9:Ic/II | 355 | 113.8 | 10 |
| 10:Id/II | 355 | 114.4 | 16 |

In the table:
PA = phthalic anhydride $$\text{max. PA yield in \% by wt.} = \frac{\text{amount of PA in g} \cdot 100}{\text{amount of pure o-xylene used in g}}$$

Running-up time=the number of days required for increasing the o-xylene loading from 0 to 80 g of o-xylene/standard $m^3$ of air

Example 11
Preparation of PA—comparison

Example 11 was carried out using a method similar to Examples 7–10 except that a 1.60 m high bed of the catalyst Ie produced for comparison as described in Example 5 was introduced into the reaction tube in place of the catalysts Ia–Id of the present invention. The maximum yield of PA, based on 100%-pure o-xylene, was 113.9% by weight at 350° C. and a running-up time of 26 days.

We claim:
1. A process for producing coated catalysts for the catalytic gas-phase oxidation of aromatic hydrocarbons to give carboxylic acids and/or carboxylic anhydrides, on the support material of which a layer comprising catalytically active metal oxides is applied in the form of a shell, wherein a powder is first produced, by spray drying or freeze drying, from a solution and/or a suspension of the catalytically active metal oxides and their precursor compounds or these precursor compounds alone in the presence or absence of auxiliaries for catalyst production, the powder is subsequently applied as a paste in the form of a shell in the presence or absence of auxiliaries for catalyst production to the support after or without prior conditioning, without prior heat treatment to generate the catalytically active metal oxides and the support coated in this way is subjected to a heat treatment to generate the catalytically active metal oxides, the average layer thickness of the active composition of the coated catalysts produced in this way being from 10 to 250 μm.

2. A process as claimed in claim 1, wherein two or more powders of different composition, produced as set forth in claim 1, are applied sequentially to the support in the form of shells, in the presence or absence of auxiliaries for catalyst production, after or without prior conditioning and without prior heat treatment to generate catalytically active metal oxides and the support coated in this way is subjected to a heat treatment to generate the catalytically active metal oxides.

3. A process as claimed in claim 1, wherein binders and/or pore formers and/or temporary activity damping agents are added as auxiliaries for catalyst production to the solution or suspension of the catalytically active metal oxides and their precursor compounds, or the precursor compounds alone, or the powder produced from this solution or suspension.

4. A process as claimed in claim 1, wherein the coated catalyst produced by coating the support with the powder comprising the catalytically active metal oxides and their precursor compounds or the precursor compounds alone and, if appropriate, auxiliaries for catalyst production is subjected before use to a heat treatment at from 250 to 450° C.

5. A process as claimed in claim 1, wherein the powder comprising the catalytically active metal oxides and their precursor compounds or the precursor compounds alone and, if appropriate, auxiliaries for catalyst production is conditioned to a particle size of from 0.1 to 100 μm before it is applied to the support.

6. A process as claimed in claim 1, wherein the catalytically active metal oxides and their precursor compounds used are, apart from titanium dioxide in the anatase form and vanadium compounds, oxides or precursor compounds of the oxides of the alkali metals, the alkaline earth metals, thallium, aluminum, zirconium, iron, nickel, cobalt, manganese, tin, silver, copper, chromium, molybdenum, tungsten, iridium, tantalum, niobium, arsenic, antimony, cerium and/or phosphorus and are applied to a support comprising quartz, porcelain, magnesium oxide, silicon carbide, tin oxide, rutile, alumina, aluminum silicate, magnesium silicate, zirconium silicate and/or cerium silicate.

7. A process for the catalytic gas-phase oxidation of aromatic hydrocarbons to give carboxylic acids and/or carboxylic anhydrides using a gas comprising molecular oxygen in a fixed bed at elevated temperature and by means of one or more coated catalysts arranged in layers in the reactor, where the support material of the coated catalysts has a layer of catalytically active metal oxides applied to it in the form of a shell, wherein use is made of at least one coated catalyst which has been produced by a process as claimed in claim 1.

8. A process as claimed in claim 7, wherein o-xylene or naphthalene is oxidized to phthalic anhydride.

9. A process as claimed in claim 7, wherein durene is oxidized to pyromellitic dianhydride.

10. A coated catalyst for the catalytic gas-phase oxidation of aromatic hydrocarbons to give carboxylic acids and/or carboxylic anhydrides, the support material of which comprises quartz, porcelain, magnesium oxide, silicon carbide, tin oxide, rutile, alumina, aluminum silicate, magnesium silicate, zirconium silicate and/or cerium silicate and has applied to it, in the form of a shell, a layer of catalytically active metal oxides which comprises, apart from titanium dioxide in the anatase form and vanadium pentoxide, oxides of the alkali metals, the alkaline earth metals, thallium, aluminum, zirconium, iron, nickel, cobalt, manganese, tin, silver, copper, chromium, molybdenum, tungsten, iridium, tantalum, niobium, arsenic, antimony, cerium and/or phosphorus, wherein the coated catalyst has been prepared by a process as claimed in claim 1.

* * * * *